United States Patent [19]

Finch et al.

[11] 3,985,641

[45] Oct. 12, 1976

[54] CATALYTIC CRACKING OF ALKANES

[75] Inventors: Jack N. Finch; Dennis L. Ripley, both of Bartlesville, Okla.

[73] Assignee: Phillips Petroleum Company, Bartlesville, Okla.

[22] Filed: Apr. 15, 1974

[21] Appl. No.: 460,937

[52] U.S. Cl. .............................. 208/121; 252/468; 252/473; 260/683 R
[51] Int. Cl.² .......................................... C10G 11/04
[58] Field of Search .................... 208/121, 119, 123; 260/683

[56] References Cited
UNITED STATES PATENTS

| | | | |
|---|---|---|---|
| 1,733,656 | 10/1929 | Egloff et al. | 208/7 |
| 1,845,439 | 2/1932 | Pier et al. | 208/112 |
| 2,211,944 | 8/1940 | Andrews et al. | 208/121 |
| 2,348,647 | 5/1944 | Reeves et al. | 208/120 |
| 2,378,530 | 6/1945 | Bailie et al. | 208/119 |
| 2,456,072 | 12/1948 | Marisic | 208/120 |
| 2,706,168 | 4/1955 | Pardee et al. | 208/119 |
| 2,886,513 | 5/1959 | Baker | 208/121 |
| 3,027,415 | 3/1962 | Steinhofer et al. | 260/683 |
| 3,215,639 | 11/1965 | Chomitz | 252/455 |
| 3,280,040 | 10/1966 | Jaffe | 252/439 |
| 3,410,787 | 11/1968 | Kubicek | 208/57 |
| 3,640,819 | 2/1972 | Watkins | 208/111 |
| 3,694,379 | 9/1972 | Yamaguchi et al. | 252/455 R |
| 3,699,037 | 10/1972 | Annesser et al. | 208/120 |
| 3,715,303 | 2/1973 | Wennerberg et al. | 208/112 |
| 3,725,495 | 4/1973 | Wrisberg et al. | 260/683 R |
| 3,767,567 | 10/1973 | Tomita et al. | 208/122 |
| 3,835,031 | 9/1974 | Bertolacini et al. | 208/120 |

*Primary Examiner*—Delbert E. Gantz
*Assistant Examiner*—G. E. Schmitkons

[57] ABSTRACT

Alkanes are catalytically cracked employing a catalyst comprising unpromoted calcium oxide or at least one alkaline earth oxide together with a promoting amount of an additional component.

7 Claims, No Drawings

CATALYTIC CRACKING OF ALKANES

BACKGROUND

The invention relates to a method for cracking alkanes.

Catalytic cracking of various hydrocarbons to provide more valuable or more useful products constitutes a very important part of refining operations. Although many catalytic cracking processes and catalysts are known, catalytic cracking is an area of continuing research in an effort to find new processes and catalysts which are more efficient, more selective to desired products, and more economical.

An object of the invention is to crack alkanes.

Another object of the invention is to crack alkanes using a catalyst.

Still another object of the invention is to provide a catalyst for cracking alkanes.

Other objects, aspects and advantages of the invention will be apparent to those skilled in the art upon studying the specification and the appended claims.

SUMMARY

According to the invention, alkanes are catalytically cracked employing a catalyst comprising unpromoted calcium oxide or at least one alkaline earth oxide together with a promoting amount of an additional component.

DETAILED DESCRIPTION OF THE INVENTION

Calcium oxide in the unpromoted form was found to be an effective catalyst for cracking alkanes. However, all the alkaline earth oxides, namely the oxides of magnesium, calcium, strontium and barium, are useful in this invention when used together with a promoting amount of an additional component. Oxides of magnesium and calcium are especially useful, although it is within the scope of the invention to include oxides of strontium and barium. The latter oxides are not preferred since effective calcination of the hydroxides from which the oxides are normally formed is difficult due to their low melting points and relatively high hydration tendencies.

Where more than one promoted alkaline earth oxide is used, the proportion of each alkaline earth oxide in the mixture is not critical and varies widely. Generally where a binary mixture is used, the amount of one alkaline earth oxide will be in the range of from about 0.1 to 50 weight percent and the other in the range of from about 99.9 to 50 weight percent. Three and four component mixtures of alkaline earth metal oxides are also within the scope of the invention.

One group of additional components found to be useful in promoting amounts in the present invention are the oxides of the Group VIB metals of the Mendeleef Periodic System. Specifically, the promoting metal oxides are selected from oxides of the group consisting of chromium, molybdenum, and tungsten. Although the precise chemical formula of this promoting species has not been determined, it is believed the oxidation state of the metal in the metal oxide is among the higher oxidation states available. In any event, this promoted form of the catalyst of the invention is the reaction product resulting from admixture of suitable alkaline earth oxides and Group VIB metal oxides under suitable catalyst-forming and catalyst-activating conditions.

The amount of promotor used in combination with the alkaline earth oxide varies widely. From 0.1 to 30 parts by weight of Group VIB metal per 100 parts by weight alkaline earth oxide or mixture thereof is generally adequate to produce the desired results. Good results were obtained using from about 1 to 10 parts by weight Group VIB metal oxides in combination with 100 parts by weight of the alkaline earth oxide.

In the catalyst preparation, oxides of the alkaline earth metals and the additional component, such as oxides of Group VIB metals, or compounds containing these elements which are convertible to the oxides on calcination, such as hydroxides, nitrates, carbonates, acetates, etc., are combined in any suitable catalyst-forming method. Such methods can include precipitation, coprecipitation, impregnation, dry mixing, wet mixing, and the like. The finished catalysts can be in the form of pellets, pills, agglomerates, powders, etc., depending upon the desired form for use. Before use, the catalyst is generally calcined in air at 400° to 650° C for from several minutes to ten hours or more.

Where it is desired to use a catalyst of the invention consisting of one or more of the promoted alkaline earth oxides, the following preparation procedure is useful.

A weighed amount of an alkaline earth oxide or an alkaline earth compound convertible to the oxide, such as hydroxide, is dry blended with a weighed amount of another such alkaline earth compound or a promoting amount of an additional component. The blend is then slurried with water after which the water is evaporated. The dried solid is compressed into discs, crushed and sieved to 16 to 60 mesh size. The catalyst is then calcined at approximately 550° C for 2 hours under dry air. Where only unpromoted calcium oxide is used, calcination of the compound as above described is generally desirable before use.

Feedstocks capable of being cracked by the catalyst system of this invention include any of the normal cracking feedstocks containing linear or branched alkanes. These can be crude oil fractions or other refinery streams. The desired mixture of products will generally determine the selection of feedstock. For example, one feedstock may be more suitable to produce gasoline than another.

Any type of reactor normally used in catalytic cracking operations can be used with the catalyst system of this invention. for example, fixed bed, fluidized bed, trickle bed, etc., reactors can be employed, though high velocity fluidized bed reactors are usually used in commercial processes.

Conditions for the catalytic cracking reaction are highly dependent upon the feedstock and desired products, Temperatures will normally range from 550° to 725° C, though temperatures from 600° to 675° C have produced good results. Space velocity of the feedstock is dependent to a large extent upon the specific conditions of the reaction, such as feedstock, temperature, diluent, desired products, etc., but a space velocity sufficient to provide a contact time of from 0.1 to 50 seconds is generally desirable. Pressures are ordinarily near atmospheric, but pressures in the range of from 0 to 200 psig can be used.

It may be desirable in some cases to employ a diluent. Inert diluents, such as nitrogen or helium gases can be used or it may be advantageous to use active gases, such as hydrogen or oxygen to control dehydrogenation, coke formation, product distribution, etc.

It is often advantageous to periodically regenerate the catalyst bed by any suitable means, such as treatment with dry air at elevated temperatures. Such regeneration generally removes deposits of coke which is formed in varying amounts during the cracking reaction.

EXAMPLES

The reactor used in the following examples was a continuous flow reactor consisting of a vertical quartz tube 1.4 cm inside diameter by 27 cm long with a total volume of 46 cc. A small diameter tube positioned in the center of the large tube contained thermocouples. The lower portion of the tube, 30 cc of volume or approximately 17 cm of length, was used for both the preheating zone and catalytic zone. After the top of the reactor was removed, a mixture of catalyst and quartz chips consisting of an equal volume of each was added to the reactor for the catalyst zone. Then an amount of quartz chips equal in volume to the above mixture was added to the reactor and thus positioned on top of the mixture to function as the preheating zone. The top of the reactor was replaced, and the feed was passed through the reactor from top to bottom.

Helium was used as the carrier gas at flow rates generally in the range 45–55 cc/min at standard conditions of temperature and pressure. A gaseous hydrocarbon feed, such as n-butane, was added to the carrier steam at a constant rate. A liquid hydrocarbon feed, such as n-heptane, was added to the carrier stream by bubbling the carrier stream through the liquid prior to entering the reactor. Partial pressures of hydrocarbons in the carrier were determined using flow rates, temperatures, etc. Unless otherwise noted in the following examples, the partial pressure of n-butane in the system was from 31 to 34 torr and that of n-heptane was 45 to 46 torr.

Reaction products and amounts thereof were determined by gas-liquid chromatography. The distribution of reaction products produced in the following examples was fairly constant. A typical distribution of products obtained by cracking n-butane is as follows:

| Product | Weight Percent |
|---|---|
| Methane | 25–40 |
| Ethane and ethylene | 25–40 |
| Propane and propylene | 15–30 |
| Carbon dioxide | 0–25 |

However, the conversion of the feed varied with the catalyst system employed, and therefore the operability of the invention is illustrated by conversion data.

EXAMPLE I

A series of runs was made employing a reactor containing only quartz chips as control runs or containing promoted and unpromoted alkaline earth oxides as the inventive runs. The results are tabulated below.

TABLE I

Cracking of n-Butane, Conversions

| Temp., °C | Quartz | | CaO | MgO | MgO/CaO 97/3 | CaO/BaO 91.5/8.5 | MgO/BaO 95/5 | Ca-Cr Oxides 5% Cr | Ca-Mo Oxides 5% Mo | | | | Mg-Mo Oxides 5% Mo | Ca-W Oxides 5% W |
|---|---|---|---|---|---|---|---|---|---|---|---|---|---|---|
| Wt. Cat. | Time, | | 7.5 gm | 5.5 gm | 5.3 gm | 7.5 gm | 5.1 gm | 1.5 gm | 1.5 gm | | 7.5 gm | | 3.2 gm | 1.14 gm |
| Run No. | Hours | 1 | 2 | 3 | 4[b] | 5 | 6 | 7 | 8 | 9 | 10[c] | 11 | 12[d] | 13[d] | 14 | 15 | 16 | 17[c] |
| 575 | 0.25 | | | 7 | 15.2 | | | | | | | 18.9 | | | | | |
| | 0.5 | 1.5 | 1.6 | | | | | | | 9.3 | | | | | | 13.2 | 5 |
| | 1 | | | 9 | 15.2 | | | | | | 3.8 | 24.2 | | | | | |
| | 2 | | | 6 | 14.0 | | | | | | | 18.3 | | | | | |
| | 3 | | | 5.2 | 14.2 | | | | | | | 15.4 | | | | | |
| | 4 | | | 7.4 | 13.7 | | | | | | | 19.5 | | | | | |
| | 5 | | | 9.2 | 13.5 | | | | | | | 17.4 | | | | | |
| | 6 | | | 9.6 | 13.9 | | | | | | | 15.0 | | | | | |
| 625 | 0.25 | 11.4 | | 19 | 41.2 | 10 | 16.4 | 20.4 | 9.8 | | | 38.3 | 72.4 | | 61.4 | | |
| | 0.5 | 8.9 | 15.2 | | | | | | | 24.9 | | | | 39.8 | | 56.9 | 20.7 |
| | 1 | | | 28.9 | 58.0 | 10.9 | 12.8 | 21.6 | 9.4 | | 23.8 | 25.9 | 65.8 | 44.4 | | 52.5 | |
| | 2 | | | 33.8 | 39.9 | 10.4 | 13.6 | 21.8 | 9.6 | | | | 52.4 | 64.9 | | 48.7 | |
| | 3 | | | 29.8 | 34.5 | 10.5 | 13.3 | 20.9 | 9.2 | | | 18 | | 64.8 | | 45.0 | |
| | 4 | | 11.2 | 23.6[a] | 17.5 | 32.6 | 10.1 | 12.7 | 20.4 | 9.7 | | | 17.3 | 32.8 | 52.8 | 40.7 | |
| | 5 | | 11.2 | | 20.5 | 32.3 | 10 | 14.4 | 20.2 | 9.8 | | | 17.4 | 27.8 | 40.8 | 36.7 | |
| | 6 | | 11.3 | | 26.8 | 29.1 | 9.7 | 14.7 | 19.7 | 9.6 | | | 16.4 | 26.4 | 30.0 | | 67.1 | 33.4 |
| 650 | 0.5 | 19 | 27 | | | | | | | 45.3 | | | | | | | |
| | 1 | | | | | | | | | | 42.4 | | | | | | |
| 675 | 0.25 | | | | | | | | | | | 59.9 | 76.5 | | | | 51.7 |
| | 0.5 | 35.9 | 45.6 | | | | | | | 41.3 | | | | | | | |
| | 1 | | | | | | | | | | 66.1 | 60.1 | 47.1 | | | | |
| | 2 | | | | | | | | | | | 40.4 | 43.6 | | | | |
| | 3 | | | | | | | | | | | 37.8 | 41.9 | | | | |
| | 4 | | | | | | | | | | | | 42.9 | | | | |
| | 5 | | | | | | | | | | | | 40.3 | | | | 66 |
| | 6 | | | | | | | | | | | | 41.7 | | | | |
| 700 | 0.5 | 53.5 | 68.2 | | | | | | | 57.6 | | | | | | | 83.6 |
| 725 | 0.1 | 75.1 | | | | | | | | | | | | | | | |
| | 0.5 | | 83.1 | | | | | | | 72.2 | | | | | | | |
| | 1 | | | | | | | | | | 89.3 | | | | | | |

[a]The flow rate for this sample was decreased from 45–55 cc/min to 22.5–27.5 cc/min at standard conditions.
[b]The flow rate for these samples was decreased from 45–55 cc/min to 22.5–27.5 cc/min at standard conditions and the partial pressure was from about 62 to 68 torr.
[c]The catalyst employed was not calcined prior to use.
[d]The catalyst employed was calcined in hydrogen.

The above runs illustrate the operability of the inventive catalysts. Runs 3 and 4 indicate the catalytic activity of unpromoted calcium oxide by comparing the conversion of these runs with runs 1 and 2 in which the reactor contained only quartz chips. Magnesium oxide, run 5, and magnesium oxide plus a minor amount of barium oxide, run 8, proved to be less effective than quartz chips and are not illustrative of the invention. Run 6 employing a major amount of magnesium oxide and a minor amount of calcium oxide, showed only a marginal improvement over quartz chips, and thus is not illustrative of the invention. Run 7 employing a major amount of calcium oxide and a minor amount of barium oxide is shown to be less effective than run 3 using calcium oxide only but more effective than the quartz control. Thus it is shown that the inventive calcium oxide catalyst can be diluted with minor amounts of other related materials and still be effective.

Runs 9 through 17 illustrate the operability of the promoted form of the catalysts and the better result obtained using these catalysts rather than quartz chips. Run 10 shows that the catalyst need not be calcined to be effective, and runs 12 and 13 show that calcining the catalyst in hydrogen produced effective catalyst.

EXAMPLE II

Another series of runs was made employing n-heptane as the feed. The results are tabulated below.

TABLE II

| Temp.,°C | | Cracking of n-Heptane | | | Ca-Mo Oxides 5% Mo |
|---|---|---|---|---|---|
| | | Quartz | CaO | MgO | |
| Wt. Cat. Run No | Time, Hours | 18 | 7.3 gm 19 | 5.3 gm 20 | 7.3 gm 21 |
| 600 | 0.25 | | | 7.5 | |
| | 2.75 | | | 5.8 | |
| | 3 | | 26.6 | | |
| | 3.75 | | | 5.0 | |
| | 4 | | 26.4 | | |
| | 4.75 | | | 5.0 | |
| | 5 | | 27 | | |
| 625 | 0.25 | 10.5 | | 16.1 | |
| | 0.33 | | 51.8 | | |
| | 1.25 | 8.2 | | | |
| | 2.5 | 20.6 | | | |
| | 2.75 | | | 18.9 | |
| | 3 | | 50.3 | | |
| | 3.75 | | | 33.8 | |

TABLE II-continued

| Temp.,°C | | Cracking of n-Heptane | | | Ca-Mo Oxides 5% Mo |
|---|---|---|---|---|---|
| | | Quartz | CaO | MgO | |
| Wt. Cat. Run No | Time, Hours | 18 | 7.3 gm 19 | 5.3 gm 20 | 7.3 gm 21 |
| | 4 | | 46.9 | | |
| | 4.75 | | | 46.2 | |
| | 5 | | 44.2 | | 39.4[a] |
| 640 | 0.25 | 43.5 | | | |
| 650 | 2.75 | 50.4 | | | |
| | 3.75 | 50.5 | | | |
| | 4.75 | 43.8 | | | |

[a]Included 2.3 cc/min dry air in carrier and feed stream.

The above data illustrates the operability of the invention employing n-heptane as the feed, particularly the samples of run 19 taken at 625° C.

What is claimed is:

1. A method for catalytically cracking alkanes comprising contacting alkanes under cracking conditions with a catalyst consisting essentially of at least one component selected from the group consisting of unpromoted calcium oxide and an alkaline earth oxide together with a promoting amount of an additional component selected from the group consisting of chromium, molybdenum, and tungsten oxide.

2. The method of claim 1 wherein the amount of promotor is in the range of from about 0.1 to 30 parts by weight per 100 parts by weight alkaline earth oxide.

3. The method of claim 1 wherein the amount of promotor is in the range of from about 1 to 10 parts by weight per 100 parts by weight alkaline earth oxide.

4. The method of claim 1 wherein the alkanes are catalytically cracked in the absence of added hydrogen.

5. The method of claim 1 wherein the cracking temperature is in the range of from about 550° to 775° C; wherein the cracking pressure is in the range of from about 0 to 200 psig; and wherein the feed-to-catalyst contact time is in the range of from about 0.1 to 50 seconds.

6. The method of claim 1 wherein said catalyst is calcined prior to contacting the alkanes at a temperature in the range of from about 400° to 650°C for a period of time in the range of from about 10 minutes to 10 hours.

7. The method of claim 6 wherein said catalyst is calcined in the presence of a gas selected from the group consisting of air, nitrogen, helium, oxygen, and hydrogen.

* * * * *